United States Patent [19]

Nakano

[11] Patent Number: 4,842,846

[45] Date of Patent: Jun. 27, 1989

[54] SUPEROXIDE DISMUTASE COMPOSITION FOR PERIODONTAL USE

[76] Inventor: Minoru Nakano, 7-9 Otemachi-3-chome, Maebashi-shi, Gunma-ken, Japan

[21] Appl. No.: 123,286

[22] Filed: Nov. 20, 1987

[30] Foreign Application Priority Data

Nov. 22, 1986 [JP] Japan .................................. 61-279497

[51] Int. Cl.$^4$ .......................... A61K 7/28; A61K 7/16; A61K 9/68; A61K 7/22
[52] U.S. Cl. ....................................... 429/50; 424/49; 424/48; 424/53; 424/54; 424/464; 424/94.4; 514/900; 514/901; 514/902
[58] Field of Search .................................... 424/49–58, 424/48, 94.4, 464; 514/900–902

[56] References Cited

U.S. PATENT DOCUMENTS 3,997,402  12/1976  Michelson ............................ 435/822
4,680,309  7/1987  Maurer ................................. 514/499

FOREIGN PATENT DOCUMENTS 0069504  5/1980  Japan .

OTHER PUBLICATIONS

Stedman's Medical Dictionary, 23rd ed, The Williams & Wilkins Co., Baltimore, U.S.A., 1976, p. 1057.
Metzler, Biochemistry, The Chemical Reactions of Living Cells, Academic Press, Inc., 1977, p. 571.
Stedman's Medical Dictionary, 24th ed., Williams and Wilkins, Baltimore, U.S.A. 1982, pp. 1061, 1371.

Primary Examiner—Howard E. Schain
Assistant Examiner—F. T. Moezie
Attorney, Agent, or Firm—Lorusso & Loud

[57] ABSTRACT

The disclosed compositions for periodontal use are characterized by inclusion of superoxide dismutase, as an active ingredient, in combination with an orally acceptable carrier. Periodontal diseases, in particular alveolar pyorrhea, may be treated and/or prevented by application of superoxide dismutase to oral cavity tissue.

19 Claims, No Drawings

SUPEROXIDE DISMUTASE COMPOSITION FOR PERIODONTAL USE

BACKGROUND OF THE INVENTION

This invention relates to a composition for periodontal use, which is characterized by containing superoxide dismutase, and provides a composition for periodontal use which can be applied for treatment and/or prevention of periodontal diseases, in particular alveolar pyorrhea.

Recently, the periodontal diseases are greatly increasing, and, according to the dentists in general practice, it is said that three in ten cases in their thirties already have the initial symptoms of alveolar pyorrhea. The initial symptoms begin with a damage of the keratine layer. Gums begin to bleed on biting an apple and tooth brushing, often accompanied by a foul breath. Healthy gingivae are usally pink-colored and stiff, whereas, in the initial stage of periodontal lesions, the gingivae deepen in red color of the margine, sometimes into dark red, increase in thickness with swelling, and bleed only with a slight touch. The exact mechanism in the progress of periodontal diseases is not known, however, it is assumed that a proliferation of anaerobic bacteria occurs in the lesions which then proceeds to alveolar pyorrhae. Alveolar pyorrhae also proceeds without cease, followed by pocket formation, increase in flail of tooth and final loss of tooth. Loss rate of teeth due to such periodontal diseases increases with age, exceeds the loss rate by cariosity in the forties and reaches the maximum in the sixties. In other words, periodontal diseases jeopardize the booth life and, consequently, the health life in the aged.

The current dietary habit, a preferance for cooked or processed food over natural food, may affect to a considerable degree, the morvidity rate of periodontal diseases. For prevention of periodontal diseases, there have been emphasized and need of regular cleaning of dental plaque and periodical elimination of dental calculus a well as stimulation and massage of gingivae. However, regular and strict execution of the above is not necessarily easy in daily life.

In addition, many other means have been reported for prevention of periodontal diseases, for example, application of various kinds of antibacterial agents, enzymes that decompose glucagon which may be responsible for dental plaque formation, and electrolytes as an astringent for ginigivae. However, none of these have been used successfully for prevention of periodontal diseases. Although these means have been also tried for treatment of alveolar pyorrhae, they are no better than an auxiliary therapy to surgical operation, and no drug, which is effective as a treating agent for alveolar pyorrhae, has yet been found. For an effective treatment of alveolar pyorrhae, we have no recourse other than surgical operations such as scaling, pocket curettage, gingivectomy, flap operation and others.

Now especially when we are moving toward an extremely aged society, the development of a simple and non-surgical method for prevention and/or treatment of periodontal diseases, in particular alveolar pyorrhae is a growing major need. Accordingly, an object of the present invention is to provide an effective and simple method for prevention and/or treatment of periodontal diseases, in particular alveolar pyorrhae. Another object of the present invention is to prolong tooth life.

SUMMARY OF THE INVENTION

I have found that, by applying superoxide dismutase to the lesion, periodontal diseases, in particular alveolar pyorrhae can be improved or recovered greatly, and that, by applying superoxide dismutase to gingivae, periodontal diseases can be prevented. Thus, the present invention concerns a composition for periodontal use, which contains superoxide dismutase as an active ingredient, in combination with an orally acceptable carrier. The present invention also includes the method for treating or preventing periodontal diseases, in particular alveolar pyorrhae, which is characterized by using superoxide dismutase or a composition as described above.

The process of manufacturing superoxide dismutase is known from many literatures and patents. For example, it can be manufactured by extraction and purification from various organs such as liver, erythrocyte and placenta of animal such as bovine or human; bacteria such as Escherichia coli, and genetically manipulated cells.

Superoxide dismutase has been suggested for use as a therapeutic agent for osteoarthitis, rhumatoid arthritis and irradiation injury which are assumed to be caused by tissue damage due to superoxide. However, its half life in blood is as short as 6 minutes, and success in safe and effective treatment of human diseases has not yet been reported. Of course, there are no reports which suggest the application of superoxide dismutase to alveolar pyorrhae as in the present invention.

DESCRIPTION OF THE PREFERRED EMBODIMENTS

Superoxide dismutase to be employed for the purpose of the present invention, may be any type of superoxide dimutase, and is not limited by its source, manufacturing process or other such considerations. Unless the activity of superoxide dismutase is impaired, any active portion of the enzyme and a modified superoxide dimutase canbe used in the present invention and are included in the term "superoxide dismutase" used in this specification. However, bovine or human superoxide dismutase is preferable.

The content of superoxide dismutase in the present composition depends on the form selected. Since superoxide dismutase displays the effect of interest in an extremely small amount, the content in ready-to-use composition is generally in the range between about $1 \times 10^{-4}$ weight percent and about 1 weight percent based on the total weight of the composition (between about $3 \times 10^{-8}$ and about $3 \times 10^{-4}$ molar percent). When it is used for prevention, a lower concentration of superoxide dismutase can be employed.

On applying superoxide dismutase to gingivae, it may be assumed to resolve superoxide to hydrogen peroxide. The latter may then react with chlorine ion to form hydrochlorite. Therefore, it must be advantageous to include catalase and one or more amino acids or derivatives thereof in the present composition in order to remove hydrogen peroxide and hypochlorite, respectively. For this purpose, commercially available catalase can be generally added in the concentration range between about $1 \times 10^{-4}$ and about 1 weight percent to the composition. Amino acids or derivatives thereof can be selected from taurine, glycine, aspartic acid, histidine, lysine and acyl glutamic acid. Taurine is most preferable. The content of amino acids or derivatives thereof in the present composition can be generally within the range from about 0.05 to about 5 weight percent.

The present composition for periodontal use, containing superoxide dismutase as an active ingredient, can be processed into any conventional form which is applied to gingivae. The effect of superoxide dismutase in treatment of periodontal diseases, in particular alveolar pyorrhae, can be expected by injecting or infusing its solution into periodontal areas or pockets or sousing them in its solution. Thus, the composition of the present invention can be preferably in a form of solution for injection or infusion, or such as mouth wash. In order to keep superoxide dismutase in contact with gingivae for a sufficient time, it may be in the form of a tablet, especially a tablet adhesive to gingivae, or chewing-gum. Further, it may be an oil or emulsion type ointment or gel formulation, which can be applied to or rubbed into gingivae. The form suitable especially for the purpose of prevention, is a conventional form of dentifrice such as paste, powder or semi-paste. For example, superoxide dismutase can be introduced in a conventional dentifrice.

Superoxide dismutase is stable against heat, has optimum pH range of about 7 to 9 and stable pH range of about 6 to 11. It is inactivated only in the presence of a strong acid or alkali, or a potent chelating agent. Thus, in manufacturing the present composition, any non-toxic conventional base and any conventional method well-known in the art can be employed. Moreover, the present composition can include any other conventional active ingredient or adjuvant ingredient, such as various kinds of enzymes, fluorine compounds, antibiotics, vitamin and others.

The present composition of injection or infusion can be manufactured by dissolving superoxide dismutase and optionally methylcellulose, sorbitol, serum albumin, preservatives and a flavoring agent, and after sterilization, filling the solution into ampules or vials. It may be a lyophilized form.

Mouth-wash can be produced by a conventional method employing optionally boric acid, borax and aluminium potassium sulfate. Favoring agents, sweetening agents or preservatives can be added.

Tablets can be produced by a conventional method employing superoxide dismutase, and optionally the following ingredients: diluting agents, binding agents, flavoring agents, coloring agents, lubricants, preservatives, sweetening agents and others. Examples of the diluting agent are various kind of cellurose ethers, acrylate polymers, starch, dextrin, milk sugar, sorbitol and calcium phosphate. Examples of the binding agent are starch, dextrin, gelatin, tragacanth and others. Further addition of polyvinyl alcohol can confer adhesiveness to the tablet.

Chewing-gum can be produced by a conventional method, employing a gum base such as vinyl acetate polymer, and binding agents, diluting agents, flavoring agents, coloring agents, preservatives and sweetening agents as described above in connection with tablets.

Ointment or gel formulations of the present invention can be produced employing a suitable base and additives depending on the properties and form desired. Examples of the base are water, glycerol, 1,3-butanediol, propylene glycol, polyethylene glycol, polypropylene glycol, ethanol, various kinds of cellulose ethers, polyvinyl alcohol, carboxyvinyl alcohol, cetyl alcohol, vaseline and liquid paraffin. If necessary, tensides such as polyoxyethylene sorbitan fatty ester, polyoxyethylene fatty ester, polyoxyethylene alkyl ether and others can be combined in the preparation. Further, there may be added a flavoring agent, coloring agent, preservative and sweetening agent.

Dentifrices of the present invention can be produced employing a suitable base and additives depending on the properties and form desired. Examples of the base suitable for preparing paste, powder or semi-paste, are calcium phosphate, calcium carbonate, aluminium hydroxide, insoluble metaphosphoric acid, calcium pyrophosphate, magnesium carbonate, silicic acid and salts thereof and pulverized polymer. In addition, wetting agents such as glycerol, sorbitol, propylene glycol, polyethylene glycol and others, and binding agents such as bentonite, sodium carboxmethylcellulose, hydroxyvinyl polymer and tragacanth gum can be used. Furthermore, if necessary, tensides such as alkylsulfate, alkylsulfonate, glycerol fatty acid ester, sorbitan fatty ester, flavoring agents, sweetening agents, coloring agents and preservatives can be added.

The present composition can be used at any stage of the periodontal disease for the purpose of treatment. The efficacies of the present composition and method are apparent from the clinical studies using twenty patients with alveolar pyorrhae. After dental calculus was removed briefly with an ultrasonic scaler, a superoxide dismutase solution (Concentration: $0.5 \times 10^{-6}$ or $1.0 \times 10^{-6}$M) was filled into the pockets, which were then curetted slightly with a scaler. Next, the patients brushed their teeth and gingivae with a tooth-brush immersed in the above superoxide dismutase solution, and maintained for a while, a pose allowing the solution to remain filled in the pockets. This therapy was repeated once a week for three weeks.

In this clinical study, all in twenty cases showed a remarkable improvement of the alveolar pyorrhae. That is, the depth of pocket is measured by a pocket probe, decreased from the average of 8.0 mm before treatment, to the average of 2.5 mm (range: 1–5 mm) after three treatments (normal value: 1–2 mm). In most caes, violet or dark red colored gingivae was improved to pink-colored only one week after the first therapy. Subjective conditions such as pain and objective syndromes such as flail of tooth were also eliminated. No side effects were observed in any case.

It is surprising that alveolar pyorrhae, the disease, an effective conservative therapy of which was not previously known, was improved within a relatively short period, by using only an extremely small amount of superoxide dismutase.

For the purpose of prevention, the use of superoxide dismutase in the form of usual dentifrices is preferable.

The present invention will be further illustrated in detail in the following examples without limiting the scope of the present invention as claimed.

Example 1: Solution for infusion

| Component | per 100 ml |
| --- | --- |
| Superoxide dismutase | 0.003 g |
| Methylcellulose | 3 g |
| Sorbitol | 10 g |
| Purified water | add to 100 ml |

In purified water, methylcellulose is slowly added to give a homogenerous solution, which is then added with the rest of the components. After adjusting the total volume, the solution is filtered through a milipore filter for sterilization, and filled into a suitable vial. Pale blue solution is obtained.

Example 2: Solution for injection

Solution for infusion, containing in addition to the components as in the solution of Examples 1, catalase (0.01 g/100 ml) and taurine (1 g/100 ml), is prepared in the same manner as described in Example 1.

Example 3: Lyophilized preparation

Superoxide dismutase (0.01 g) is dissolved in 0.5% human serum albumin solution and the total volume is adjusted ot 100 ml. Each 3 ml of the solution is filled into a 10 ml vial, and lyophilized. Prior to use, 10 ml of water is added to reproduce an infusible solution.

Example 4: Tablet

| Component | per 1 tablet |
|---|---|
| Superoxide dismutase | 0.001 mg |
| Microcrystalline cellulose | 120 mg |
| Magnesium stearte | 1.5 mg |
| Polyvinyl alcohol | 30 mg |
| Pectin | 9 mg |
| Hydrogenated oil | 3 mg |
| Milk sugar | 136.5 mg |
| Total | 300.0 mg |

The above components are mixed thoroughly and compressed to obtain a plain tablet. Since this solution has an adhesiveness to the gingivae, it can be maintained in the mouth, releasing superoxide dismutase slowly.

Example 5: Tablet

Tablets containing, in addition to the components as in the tablet of Example 4, catalase (0.01 mg/tablet) and taurine (10 mg/tablet), are prepared in the same manner as described in Example 4.

Example 6: Oil Type ointment

| Component | per 100 mg |
|---|---|
| A: Superoxide dismutase | 0.003 g |
| Purified water | 1.0 g |
| Propylene glycol | 1.0 g |
| B: Polyvinyl alcohol | 5.0 g |
| Liquid paraffin | 40.0 g |
| White vaseline | add to 100 g |

Components B are combined and melted by heating to the temperature 70°–75° C. on a water bath and, after cooling to 45°–50° C., added with Components A under stirring to produce a homogenous oil type ointment.

Example 7: Emulsion type ointment

| Components | per 100 g |
|---|---|
| A: Superoxide dismutase | 0.01 g |
| B: Stearyl alcohol | 5.0 g |
| White vaseline | 8.0 g |
| Liquid paraffin | 8.0 g |
| Polyoxyethylene(20)sorbitan monostearate | 4.0 g |
| Sorbitan monostearate | 2.0 g |
| Glycerol fatty ester | 4.0 g |
| Butyl p-hydroxybenzoate | 0.05 g |
| C: Methyl p-hydroxybenzoate | 0.1 g |
| Citric acid | 0.04 g |

| Components | per 100 g |
|---|---|
| Propylene glycol | 10.0 g |
| Purified water | add to 100 g |

Components B are combined and melted by heating to a temperature of 70°–75° C. and added with Components C which were preheated to 70°–75° C. under stirring to obtain an emulsion. After stirring for 15 minutes, the emulsion is cooled to 50° C. with water and added with Components A, which had been dissolved in a part of purified water, under stirring to produce a homogeneous emulsion type ointment.

Example 8: Emulsion type ointment

By the procedure analogous to Example 7, but Component A further included 0.01 g of catalase and Components B 1 g of taurine, an emulsion type ointment is manufactured.

Example 9: Aqueous gel

| Component | |
|---|---|
| A: Superoxide dismutase | 0.003 g |
| Taurine | 1.0 g |
| B: Carboxyvinyl polymer | 1.0 g |
| C: Sodium hydroxide | q.s. |
| D: Glycerol | 10.0 g |
| Ethanol | 3.0 g |
| Purified water | add to total 100 g |

The mixture of components D is slowly added to and dispersed homogeneously into component B. To this dispersion, component A dissolved in purified water is added and homogeneously dissolved. The pH of the dispersion is adjusted to 6.5 with sodium hydroxide to obtain an aqueous gel.

Example 10: Tooth paste

| Component | per 100 g |
|---|---|
| A: Superoxide dismutase | 0.001 g |
| Sodium lauryl sulfate | 2.0 g |
| Sodium lauroyl sarcosinate | 0.2 g |
| Calcium hydrogen phosphate | 40.0 g |
| Magnesium phosphate | 0.5 g |
| Silicic anhydride | 2.0 g |
| B: Glycerol | 15.0 g |
| Sorbitol | 10.0 g |
| Sodium lactate | 2.0 g |
| Carboxymethylcellulose | 1.0 g |
| Methyl p-phydroxybenzoate | 0.05 g |
| Ethyl p-hydroxybenzoate | 0.05 g |
| Perfume | q.s |
| Purified water | add to total 100 g |

Components of the above B except perfume are mixed into a homogeneous solution. This solution is combined with components of the above A successively under kneading. Finally perfume is added to obtain a homogeneous tooth paste of this invention.

I claim:

1. A composition for the treatment or prevention of periodontal disease by application to oral cavity tissue, said composition comprising: (1) superoxide dismutase in an amount sufficient for said treatment or prevention and (2) catalase in an amount sufficient to remove hydrogen proxide.

2. A composition according to claim 1, wherein said superoxide dismutase is human superoxide dismutase.

3. A composition according to claim 1, wherein said superoxide dismutase is bovine superoxide dismutase.

4. A composition according to claim 1, wherein the amount of superoxide dismutase is within the range of from about $1 \times 10^{-4}$ weight percent to about 1 weight percent based on the total weight of the composition.

5. A composition according to claim 4, wherein the amount of said catalase is within the range of from about $1 \times 10^{-4}$ to about 1 weight percent based on the total weight of the composition.

6. A composition according to claim 1, further comprising one or more amino acids or derivatives thereof.

7. A composition according to claim 1, further comprising an amino acid or derivative thereof selected from the group consisting of taurine, glycine, aspartic acid, histidine, lysine and acyl glutamic acid.

8. A composition according to claim 6, wherein the amount of said amino acid or derivative thereof is within the range of from about 0.05 weight percent to about 5 weight percent based on the total weight of the composition.

9. A composition according to claim 1 in the form of a tablet, chewing gum, ointment, gel, mouthwash, or dentifrice.

10. A composition according to claim 1, wherein said composition is in the form of a solution for injection or infusion.

11. A composition according to claim 1, wherein said composition is in the form of a mouth-wash.

12. A composition according to claim 1, wherein the form is a tablet or chewing-gum.

13. A composition according to claim 1, wherein said composition is in the form of a tablet adhesive to gingivae.

14. A composition according to claim 1, wherein said composition is in the form of an oil type or emulsion type ointment.

15. A composition according to claim 1 wherein said composition is a dentifrice in the form of a paste, powder or semi-paste.

16. A method for treating or preventing periodontal disease comprising applying superoxide dimutase, in an amount sufficient for treating or preventing periodontal disease, to oral cavity tissue.

17. A method of claim 16, wherein said superoxide dismutase is topically applied.

18. The method of claim 16, wherein said superoxide dismutase is injected or infused into the oral cavity tissue.

19. The method of claim 16 wherein the superoxide dismutase is applied in admixture with catalase wherein said catalase is in an amount sufficient to remove hydrogen peroxide.

* * * * *

UNITED STATES PATENT AND TRADEMARK OFFICE
CERTIFICATE OF CORRECTION

PATENT NO. : 4,842,846

DATED : June 27, 1989

INVENTOR(S) : Minoru NAKANO

It is certified that error appears in the above-identified patent and that said Letters Patent is hereby corrected as shown below:

Col. 1, line 34, "booth" should read --tooth--;

line 40, "and" should read --the--;

line 41, "periodical" should read --periodic--; and line 42, "a" should read --as--.

Col. 2, line 41, "canbe" should read --can be--;

line 48, after "in" insert --a--.

Col. 3, line 50, "cellurose" should read --cellulose--.

Col. 4, line 5, "preserative" should read --preservative--;

line 16, "carboxmethylcellulose" should read --carboxymethylcellulose--;

line 43, "caes" should read --cases--.

line 68, "homogenerous" should read --homogeneous--.

UNITED STATES PATENT AND TRADEMARK OFFICE
CERTIFICATE OF CORRECTION

PATENT NO. : 4,842,846
DATED : June 27, 1989
INVENTOR(S) : Minoru NAKANO

It is certified that error appears in the above-identified patent and that said Letters Patent is hereby corrected as shown below:

Col. 5, line 13, "0.5%" should read --5%--;

line 24, "stearte" should read --stearate--.

Col. 6, line 68, "proxide" should read --peroxide--.

Signed and Sealed this

Twenty-fourth Day of April, 1990

Attest:

HARRY F. MANBECK, JR.

*Attesting Officer*  *Commissioner of Patents and Trademarks*